United States Patent
Koketsu et al.

(10) Patent No.: US 7,176,164 B2
(45) Date of Patent: Feb. 13, 2007

(54) 1,3-SELENAZOLIN DERIVATIVES AND PROCESS FOR PREPARING THE SAME

(75) Inventors: Mamoru Koketsu, Gifu (JP); Hideharu Ishihara, Gifu (JP)

(73) Assignee: Gifu University, Gifu (JP)

( * ) Notice: Subject to any disclaimer, the term of this patent is extended or adjusted under 35 U.S.C. 154(b) by 88 days.

(21) Appl. No.: 10/318,869

(22) Filed: Dec. 13, 2002

(65) Prior Publication Data
US 2003/0158239 A1 Aug. 21, 2003

(30) Foreign Application Priority Data
Dec. 25, 2001 (JP) ............................ 2001-392861

(51) Int. Cl.
*A61K 31/41* (2006.01)
*C07D 293/06* (2006.01)
*A01N 55/00* (2006.01)

(52) U.S. Cl. .................. 504/261; 514/359; 548/100

(58) Field of Classification Search ............... 548/100; 514/359; 504/261
See application file for complete search history.

(56) References Cited

OTHER PUBLICATIONS

Database CAS Online on STN, Chem. Abstr., Accession No. 1973:515502, Shvaika et al., Khimiya Geterotsiklicheskikh Soedinenii (1973(, (7), 930-3, abstract.*
Database CAS Online on STN, Chem. Abstr., Accession No. 1981:480838, Levshin et al., Khimiko-Farmatsevticheskii Zhurnal (1981), 15(4), 27-31, abstract.*
Database CAS Online on STN, Chem. Abstr., Accession No. 1985:578205, Levshin et al., Zhurnal Organicheskoi Khimi (1985), 21(3), 641-4, abstract.*
Giudicelli J-F et al.; "Sur la tautomérie phényl-5 amino-2 ou méthylamino-2 sélénazolinons-4<=>phényl-5 imino-2 ou méthylimino-2 sélénazolidinones-4"; Comptes Rendus Hebdomadaires Des Seances De L' Academie Des Sciences, Serie C: Sciences Chimiques, vol. 262; Jan. 17, 1966; pp. 285-288.
Giudicelli, J-F et al.; "Sur la tautomérie phenyl-5 amino-2 sélénazolinones-4 <=> phenyl-5 inimo-2 sélénazolidinones-4"; Bulletin de la Societe Chimique de France, No. 3; 1968; pp. 1099-1106.
Comrie A M et al; "Tautomerism of 2-iminoselenazolidin-4-ones"; Journal of the Chemical Society, Dec. 1963; pp. 5713-5717.
Koketsu M et al.; "Facile preparation of 2-imino-1, 3-selenazolidin-4-one derivatives by reaction of N,N'-disubstituted selenoureas with alpha-haloacyl halides"; SYNTHESIS No. 2, Feb. 1, 2002; pp. 195-198.

Potts K T et al.; "Mesoionic compounds 41. Anhydro-4-hydroxy-2, 3, 5-trisubstituted-1, 3-selenazolium hydroxides and anhydro-4-hydroxy-6-oxo-2,3,5-trisubstituted-4H-1,3-selenazinium hydroxides"; Journal of Organic Chemistry, vol. 42, No. 9; Apr. 29, 1977; pp. 1644-1648.
Potts K T et al.; "Mesoionic compounds 39. Synthesis of some functionally substituted five-membered systems using 1,2-bielectrophiles as cyclization agents"; Journal of Organic Chemistry, vol. 42, No. 9; Apr. 29, 1977; pp. 1633-1638.
Koketsu M et al.; "1,3-Selenazine derivatives induce cytotoxicity and DNA fragmentation in human HT-1080 fibrosarcoma cells"; European Journal of Pharmaceutical Sciences, vol. 9, No. 2, Dec. 1999; pp. 157-161.
Database Caplus 'Online! Chemical Abstracts Service, Columbus, Ohio, US; vol. 41; No. 10; 1975; 1 Page.
Database Crossfire Beilstein 'Online! Beilstein Institut zur Förderung der Chemischen Wissenschaften, Frankfurt am Main, DE, vol. 17, No. 5; 1969; 1 Page.
Comrie A M et al. "Some 2-iminoselenazolidin-4-ones and related compounds"; Journal of Pharmacy and Pharmacology; vol. 16, 1964; pp. 268-272.
Cho S I et al.; "Novel compounds, '1-3selenazine derivatives' as specific inhibitors of eukaryotic elongation factor-2 kinase"; Biochimica et Biophysica Acta, vol. 1475; No. 3; Jul. 26, 2000; pp. 207-215.
Chemical and Pharmaceutical Bulletin, vol. 17, nr. 5, 1969, pp. 910-919.

* cited by examiner

*Primary Examiner*—Joseph K. McKane
*Assistant Examiner*—Rebecca Anderson
(74) *Attorney, Agent, or Firm*—Boyle Fredrickson Newholm Stein & Gratz S.C.

(57) ABSTRACT

A process for preparing novel 1,3-selanazolin derivatives represented by chemical formula 1 at high yield. This process includes a step of reacting a selenourea and an α-haloacyl halide in a solvent and in the presence of a catalyst (1)

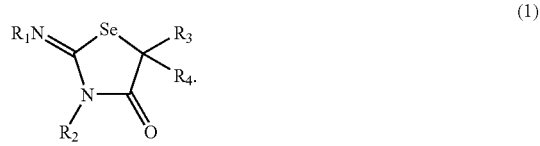

10 Claims, No Drawings

1,3-SELENAZOLIN DERIVATIVES AND PROCESS FOR PREPARING THE SAME

BACKGROUND OF THE INVENTION

The present invention relates to novel compounds in the form of 1,3-selenazolin derivatives, which can be used as raw materials of medicaments and agricultural chemicals, and a process for preparing the same.

Since heterocyclic compounds containing selenium atom have numerous physiological activities, they are considered to be extremely important compounds. The following references disclose conventional processes for preparing selenium-containing heterocyclic compounds using selenoureas.

(a) Maslankiewicz, A.; Skrzypek, L.; Niedbala, A. *Pol. J. Chem.* 1996, 70, 54.
(b) Keil, D.; Hartmann, H., *Phosphorus, Sulfur Silicon Relat. Elem.* 1999,152, 169.
(c) Shafiee, A.; Ebrahimzadeh, M. A.; Maleki, A. *J. Heterocycl. Chem.* 1999,36, 901.
(d) Koketsu, M.; Suzuki, N.; Ishihara, H. *J. Org. Chem.,* 1999, 64, 6473.
(e) Zhou, Y.; Linden, A.; Heimgartner, H., *Helv. Chim. Acta* 2000, 83, 1576.
(f) Attanasi, O. A.; Filippone, P.; Guidi, B.; Perrulli, F. R.; Santeusanio, S. *Synlett,* 2001, 144.

However, since the conventional processes use chloroacetic acid for the starting material, the structures of the compounds prepared by the conventional processes differ from the 1,3-selenazolin derivatives of the present invention explained below. As is described in the above references, since chloroacetic acid has lower reactivity than α-haloacyl halides, the processes of the prior art did not allow the production of selenium-containing heterocyclic compounds at high yield.

SUMMARY OF THE INVENTION

The object of the present invention is to provide novel 1,3-selenazolin derivatives having satisfactory physiological activity. Another object of the present invention is to provide a process for preparing highly reactive 1,3-Selenazolin derivatives easily and at high yield.

To achieve the above object, the present invention provides 1,3-Selenazolin derivatives represented by the following chemical formula 1.

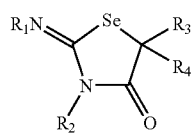

(1)

A further perspective of the present invention is a process for preparing 1,3-selenazolin derivatives. The process includes reacting a selenourea represented by the following chemical formula 2 with an α-haloacyl halide represented by the following chemical formula 3 in a solvent and in the presence of a catalyst.

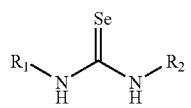

(2)

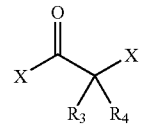

(3)

Other aspects and advantages of the present invention will become apparent from the following description, taken in conjunction with the accompanying drawings, illustrating by way of example the principles of the invention.

DETAILED DESCRIPTION OF THE PREFERRED EMBODIMENT

The following provides a detailed explanation of an embodiment of the present invention.

The present invention provides the novel 1,3-selenazolin derivatives represented by chemical formula 1, and their preparation process.

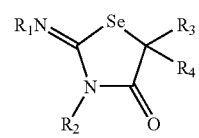

(1)

In chemical formula 1, $R_1$, $R_2$, $R_3$ and $R_4$ denote one of hydrogen, alkyl group having 1 to 30 carbon atoms, cycloalkyl group having 1 to 30 carbon atoms, alkynyl group having 1 to 30 carbon atoms, aryl group having 1 to 30 carbon atoms, alkoxide group having 1 to 30 carbon atoms, acyl group having 1 to 30 carbon atoms, alkylthio group having 1 to 30 carbon atoms, arylthio group having 1 to 30 carbon atoms and alkoxycarbonyl group having 1 to 30 carbon atoms. $R_1$, $R_2$, $R_3$ and $R_4$ may all be hydrogen. At least one of $R_1$, $R_2$, $R_3$ and $R_4$ may be substituted with a functional group other than hydrogen. In the case two or more of $R_1$, $R_2$, $R_3$ and $R_4$ are substituted with functional groups other than hydrogen, the substitution groups may be mutually the same or different. 1,3-Selenazolin derivatives in which $R_1$, $R_2$, $R_3$ and $R_4$ are selected from hydrogen, alkyl groups having 2 to 8 carbon atoms and cycloalkyl groups having 2 to 8 carbon atoms are preferable since they can be easily produced.

The 1,3-selenazolin derivatives of the present embodiment are prepared by reacting a selenourea represented by chemical formula 2 with an α-haloacyl halide represented by chemical formula 3 in a solvent and in the presence of a catalyst.

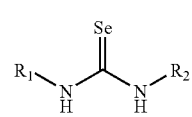

(2)

In chemical formula 2, $R_1$ and $R_2$ denote one of hydrogen, alkyl group having 1 to 30 carbon atoms, cycloalkyl group having 1 to 30 carbon atoms, alkynyl group having 1 to 30 carbon atoms, aryl group having 1 to 30 carbon atoms, alkoxide group having 1 to 30 carbon atoms, acyl group having 1 to 30 carbon atoms, alkylthio group having 1 to 30 carbon atoms, arylthio group having 1 to 30 carbon atoms, and alkoxycarbonyl group having 1 to 30 carbon atoms. $R_1$ and $R_2$ may both be hydrogen. At least one of $R_1$ and $R_2$ may be substituted with a functional group other than hydrogen. In the case $R_1$ and $R_2$ are substituted with functional groups other than hydrogen, the functional groups may be mutually the same or different.

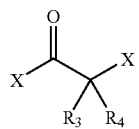

(3)

In chemical formula 3, X denotes halogen, and $R_3$ and $R_4$ denote hydrogen, alkyl group having 1 to 30 carbon atoms, cycloalkyl group having 1 to 30 carbon atoms, alkynyl group having 1 to 30 carbon atoms, aryl group having 1 to 30 carbon atoms, alkoxide group having 1 to 30 carbon atoms, acyl group having 1 to 30 carbon atoms, alkylthio group having 1 to 30 carbon atoms, arylthio group having 1 to 30 carbon atoms and alkoxycarbonyl group having 1 to 30 carbon atoms. $R_3$ and $R_4$ may both be hydrogen, and at least one of $R_3$ and $R_4$ may be substituted with a functional group other than hydrogen. In the case $R_3$ and $R_4$ are substituted with functional groups other than hydrogen, the substitution groups may be the same or different.

Selenoureas and α-haloacyl halides react according to the following reaction scheme, and hydrogen halide (HX) is produced as a by-product.

[Reaction Scheme]

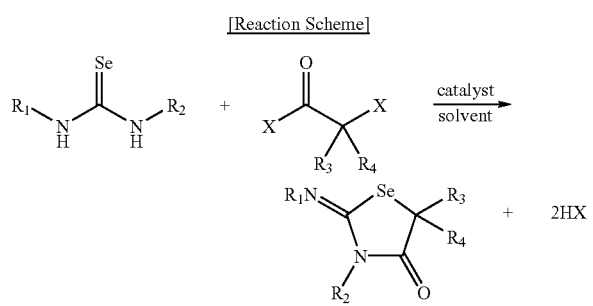

The compound of chemical formula 3 is an α-haloacyl halide having halogens at two α positions, and various substitution groups at one of the α positions. In consideration of reactivity, the halogen is preferably chlorine or bromine. Since the α-haloacyl halide of chemical formula 3 has two halogens, its reactivity is relatively high.

The selenourea of chemical formula 2 and α-haloacyl halide are industrial raw materials that can be acquired easily.

The molar ratio of the α-haloacyl halide and selenourea is preferably 1:1.5 to 1:2.0. If this molar ratio is less than 1:1.5, since the selenourea is an unstable compound, the yield of 1,3-selenazolin derivative decreases. On the other hand, if the molar ratio exceeds 1:2.0, the reaction ratio reaches nearly 100%, and it is difficult for the reaction to proceed further.

In the preparation process of the present embodiment, an ordinary catalyst used in organic synthesis chemistry is used. There are no particular restrictions on the catalyst used, and examples of catalysts that can be used include metal catalysts, Lewis acid catalysts, basic catalysts and enzymes. Among these, basic catalysts such as pyridine and triethylamine are preferable since the hydrogen halides that are produced can be captured. In the case where a catalyst is not added, the reaction between the α-haloacyl halide and selenourea hardly progresses at all. Thus, a catalyst is the essential condition for the preparation process of the present invention.

In the preparation process of the present embodiment, an ordinary reaction solvent used in organic synthesis chemistry is used. There are no particular restrictions on the solvent used, and examples of solvents that can be used include alcohols (such as methanol, ethanol, isopropyl alcohol and butanol), halogen-based solvents (such as methylene chloride, chloroform, 1,2-dichloro ethane, 1,1,2-trichloro ethane and carbon tetrachloride), ether-based solvents (such as tetrahydrofuran, diethyl ether and dimethyl ether), alkanes (such as hexane, cyclohexane and isooctane) and esters (such as ethyl acetate and methyl propionate). Preferable examples include ether-based solvents, alcohols, halogen-based solvents and alkanes. Ether-based solvents are more preferable in consideration of not inhibiting the reaction. Water is not preferable due to the poor solubility of the raw materials.

The reaction temperature is preferably −100 to 30 degrees Celsius, and more preferably −100 to 10 degrees Celsius. In the case the reaction temperature is lower than −100 degrees Celsius, the reaction rate becomes low, undesirably. On the other hand, in the case the reaction temperature is higher than 30 degrees Celsius, the reaction rate becomes excessively fast and causes side reactions to occur easily, thereby resulting in the risk of a decrease in the yield of 1,3-selenazolin derivatives, undesirably.

The 1,3-selenazolin derivatives of the present embodiment have potent physiological activity, and can be used as medicaments such as anticancer drugs, protein kinase inhibitors, antioxidants and nerve cell proliferation agents (Alzheimer's disease preventive agents), agricultural chemicals such as insecticides and herbicides and other substances such as light-sensitive agents for photographs.

The following advantages are obtained according to the present embodiment.

The 1,3-selenazolin derivatives are compounds that have a novel chemical structure heretofore unreported. The 1,3-selenazolin derivatives demonstrate satisfactory physiological activity, and can be used as, for example, medicaments such as anticancer drugs and antioxidants, or agricultural chemicals such as insecticides and herbicides. Thus, the 1,3-selenazolin derivatives of the present embodiment are extremely useful in industry.

In addition, the 1,3-selenazolin derivatives are prepared by reacting the selenourea represented by chemical formula 2 with the α-haloacyl halide represented by chemical formula 3 in a solvent and in the presence of a catalyst. Selenoureas and α-haloacyl halides are industrial raw materials that can be acquired easily, and both have high reactivity. Thus, the 1,3-selenazolin derivatives are prepared easily and at high yield.

Since the above reaction proceeds even under mild conditions of normal temperature and normal pressure, its procedure is easy and special reaction equipment is not required.

The present invention will be described below specifically by way of Examples and Test examples.

EXAMPLE 1

0.42 g (2.0 mmol) of N,N'-diisopropyl selenourea were dissolved in 20 mL of tetrahydrofuran. 0.08 mL (1.0 mmol) of chloroacetyl chloride were added to the solution, and after stirring well, the mixture was allowed to react at 0 degrees Celsius for one hour. 0.09 mL (1.0 mmol) of pyridine was then added to the reaction mixture, followed by stirring at 0 degrees Celsius for additional 2 hours. The reaction mixture was extracted by an ordinary method, washed with water and dried, and the solvent was distilled off. As a result, 0.25 g of 3-isopropyl-2-isopropylimino-1,3-selenazolidin-4-one were obtained. The purity was 98.7%, and the yield was 100%.

Elementary analysis, nuclear magnetic resonance spectrum, mass analysis and infrared absorption spectrum of 3-isopropyl-2-isopropylimino-1,3-selenazolidin-4-one were as indicated below.

Elementary analysis: (C:H:N) Calcd. 43.73, 6.52, 11.33. Found 43.70, 6.66, 11.36.

NMR (CDCl$_3$ solvent, TMS internal standard)

$^1$H-NMR: δ1.18 (6H, d, J=6.4 Hz, CH$_3$), 1.41(6H, d, J=7.6 Hz, CH$_3$), 3.14 (1H, m, CH), 3.78 (2H, s, CH$_2$, 2J($^{77}$Se-$^1$H)=12.4 Hz), 4.79 (1H, m, CH).

$^{13}$C-NMR: δ18.6, 23.6, 24.8 (1J($^{77}$Se-$^{13}$C)=60.2 Hz), 48.8, 57.5, 143.2, 173.0.

$^{77}$Se NMR (78.2 MHz, CDCl$_3$): δ226.8.

MS (CI): m/z=249 [M$^+$+1].

Infrared absorption spectrum (KBr disk): 1698, 1644 cm$^{-1}$

Thus, 3-isopropyl-2-isopropylimino-1,3-selenazolidin-4-one was confirmed to be a compound represented by chemical formula 4.

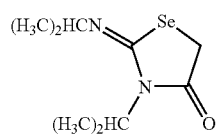

(4)

EXAMPLE 2

0.58 liter (2.0 mol) of N,N'-cyclohexyl selenourea were dissolved in 20 liter of tetrahydrofuran. 0.08 liter (1.0 mol) of chloroacetyl chloride were added to the solution, and after stirring well, the mixture was allowed to react at 0 degrees Celsius for one hour. Triethylamine (1.0 mol) was then added to the reaction mixture, followed by stirring at 0 degrees Celsius for additional 2 hours. The reaction mixture was extracted by an ordinary method, washed with water and dried, and the solvent was distilled off. As a result, 0.33 kg of 3-cyclohexyl-2-cyclohexylimino-1,3-selenazolidin-4-one were obtained. The purity was 99.7%, and the yield was 100%.

Elementary analysis, nuclear magnetic resonance spectrum, mass analysis and infrared absorption spectrum of 3-cyclohexyl-2-cyclohexylimino-1,3-selenazolidin-4-one were as indicated below.

Elementary analysis: (C:H:N) Calcd. 55.04, 7.39, 8.56. Found 55.04, 7.35, 8.36.

NMR (CDCl$_3$ solvent, TMS internal standard)

$^1$H-NMR: δ1.18 (6H, d, J=6.4 Hz, CH$_3$), 1.1–1.82 (18H, m), 2.38 (2H, qd, J=12.8 Hz, 3.2 Hz, CH$_2$), 2.84 (1H, m, CH), 3.78 (2H, s, CH$_2$, 2J($^{77}$Se-$^1$H)=16.0 Hz), 4.3–4.42 (1H, m, CH).

$^{13}$C-NMR: δ24.2, 24.8, 25.3, 25.7, 26.2, 28.0, 33.4, 57.0, 64.9, 142.9, 173.1.

$^{77}$Se NMR (78.2 MHz, CDCl$_3$): δ224.0.

MS (CI): m/z=329 [M$^+$+1]

Thus, 3-cyclohexyl-2-cyclohexylimino-1,3-selenazolidin-4-one was confirmed to be a compound represented by chemical formula 5.

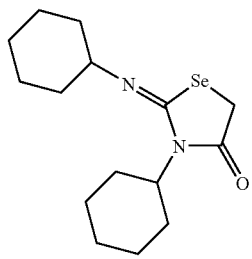

(5)

EXAMPLE 3

The reaction was carried out in the same manner as Example 1 except that chloromethylacetyl chloride (1.0 mmol) was used instead of chloroacetyl chloride for the α-haloacyl halide. As a result, 3-isopropyl-2-isopropylimino-5-methyl-1,3-selenazolidin-4-one was obtained. The yield was 100%.

Elementary analysis, nuclear magnetic resonance spectrum, mass analysis and infrared absorption spectrum of 3-isopropyl-2-isopropylimino-5-methyl-1,3-selenazolidin-4-one were as indicated below.

Elementary analysis: (C:H:N) Calcd. 45.98, 6.95, 10.72. Found 45.99, 6.99, 10.68.

NMR (CDCl$_3$ solvent, TMS internal standard)

$^1$H NMR: δ1.17, 1.18 (6H, d, J=6.4 Hz, CH$_3$), 1.40, 1.41 (6H, d, J=6.8 Hz, CH$_3$), 1.74 (3H, d, J=7.0 Hz, CH$_3$), 3.11 (1H, m, CH), 4.12 (1H, q, J=7.0 Hz, CH), 4.79 (1H, m, CH).

$^{13}$C NMR: δ18.7, 20.5, 23.6, 36.2 ($^1$J($^{77}$Se-$^{13}$C)=62.3 Hz), 48.6, 57.6, 142.4, 176.5.

$^{77}$Se NMR (78.2 MHz, CDCl$_3$) δ330.7.

MS (CI): m/z=263 [M$^+$+1].

Infrared absorption spectrum (KBr disk): 1706, 1633 cm$^{-1}$

Thus, 3-isopropyl-2-isopropylimino-5-methyl-1,3-selenazolidin-4-one was confirmed to be a compound represented by chemical formula 6.

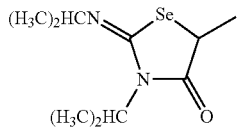

(6)

EXAMPLE 4

The reaction was carried out in the same manner as Example 1 except that bromoethylacetyl bromide (1.0 mmol) was used instead of chloroacetyl chloride for the α-haloacyl halide. As a result, 3-isopropyl-2-isopropylimino-5-ethyl-1,3-selenazolidin-4-one was obtained. The yield was 100%.

Elementary analysis, nuclear magnetic resonance spectrum, mass analysis and infrared absorption spectrum of 3-isopropyl-2-isopropylimino-5-ethyl-1,3-selenazolidin-4-one were as indicated below.

Elementary analysis: (C:H:N) Calcd. 48.00:7.32:10.18. Found 48.12:7.43:10.06

NMR (CDCl$_3$ solvent, TMS internal standard)

$^1$H NMR: δ1.01 (3H, t, J=7.2 Hz, CH$_3$), 1.17, 1.19 (6H, d, J=6.0 Hz, CH$_3$), 1.40 (6H, d, J=6.8 Hz, CH$_3$), 1.92 (1H, m, CH$_2$), 2.23 (1H, m, CH), 3.15 (1H, m, CH), 4.12 (1H, q, J=4.8 Hz, CH), 4.79 (1H, m, CH).

$^{13}$C NMR: δ11.8, 18.6, 18.8, 23.6, 27.4, 45.1 ($^1$J($^{77}$Se-$^{13}$C)=62.2 Hz), 48.5, 57.6, 142.8, 175.7.

$^{77}$Se NMR (78.2 MHz, CDCl$_3$) δ288.5.

MS (CI): m/z=277 [M$^+$+1].

Infrared absorption spectrum (KBr disk): 1702, 1644 cm$^{-1}$

Thus, 3-isopropyl-2-isopropylimino-5-ethyl-1,3-selenazolidin-4-one was confirmed to be a compound represented by chemical formula 7.

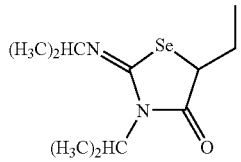

(7)

EXAMPLE 5

The reaction was carried out in the same manner as Example 1 except that bromodimethylacetyl bromide (1.0 mmol) was used instead of chloroacetyl chloride for the α-haloacyl halide. As a result, 3-isopropyl-2-isopropylimino-5,5-dimethyl-1,3-selenazolidin-4-one was obtained. The yield was 98%.

Elementary analysis, nuclear magnetic resonance spectrum and mass analysis of 3-isopropyl-2-isopropylimino-5,5-dimethyl-1,3-selenazolidin-4-one were as indicated below.

Elementary analysis: (C:H:N) Calcd. 48.00, 7.32, 10.18. Found 48.23, 7.51, 10.16.

NMR (CDCl$_3$ solvent, TMS internal standard)

$^1$H NMR: δ1.17 (6H, d, J=5.6 Hz, CH$_3$), 1.41(6H, d, J=6.8 Hz, CH$_3$), 1.74 (6H, s, CH$_3$), 3.08 (1H, m, CH), 4.80 (1H, m, CH).

$^{13}$C NMR: δ18.8, 23.6, 30.0, 47.8, 48.5, 57.7, 141.8, 179.5.

$^{77}$Se NMR (78.2 MHz, CDCl$_3$) δ429.1.

MS (CI): m/z=277 [M$^+$+1].

Thus, 3-isopropyl-2-isopropylimino-5,5-dimethyl-1,3-selenazolidin-4-one was confirmed to be a compound represented by chemical formula 8.

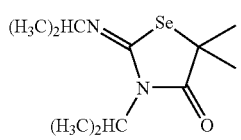

(8)

EXAMPLE 6

The reaction was carried out in the same manner as Example 1 except that chlorophenylacetyl chloride (1.0 mmol) was used instead of chloroacetyl chloride for the α-haloacyl halide. As a result, 3-isopropyl-2-isopropylimino-5-phenyl-1,3-selenazolidin-4-one was obtained. The yield was 98%.

Elementary analysis, nuclear magnetic resonance spectrum and mass analysis of 3-isopropyl-2-isopropylimino-5-phenyl-1,3-selenazolidin-4-one were as indicated below.

Elementary analysis: (C:H:N) Calcd. 50.35, 6.69, 9.79. Found 50.24, 6.69, 9.74.

NMR (CDCl$_3$ solvent, TMS internal standard)

$^1$H NMR: δ1.21, 1.22 (6H, d, J=10.0 Hz, CH$_3$), 1.44, 1.45 (6H, d, J=6.8 Hz, CH$_3$), 3.17 (1H, m, CH), 4.87 (1H, m, CH), 5.21 (1H, s, CH, 2J($^{77}$Se-$^1$H)=13.6 Hz), 7.25–7.36 (5H, m, Ar).

$^{13}$C NMR: δ18.7, 18.9, 23.6, 23.7, 45.7 ($^1$J($^{77}$Se-$^{13}$C)=62.2 Hz), 49.2, 57.6, 128.1, 128.3, 129.0, 138.3, 142.5, 174.3.

$^{77}$Se NMR (78.2 MHz, CDCl$_3$) δ381.9.

MS (CI): m/z=325 [M$^+$+1].

Thus, 3-isopropyl-2-isopropylimino-5-phenyl-1,3-selenazolidin-4-one was confirmed to be a compound represented by chemical formula 9.

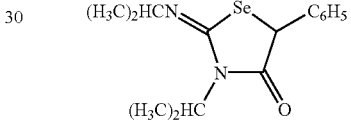

(9)

EXAMPLE 7

The reaction was carried out in the same manner as Example 1 except that N,N'-t-butyl selenourea (2.0 mmol) was used instead of N,N'-diisopropyl selenourea for the selenourea. As a result, 3-t-butyl-2-t-butylimino-1,3-selenazolidin-4-one was obtained. The yield was 88%.

Elementary analysis, nuclear magnetic resonance spectrum and mass analysis of 3-t-butyl-2-t-butylimino-1,3-selenazolidin-4-one were as indicated below.

Elementary analysis: (C:H:N) Calcd. 48.00, 7.32, 10.18. Found 48.12, 7.38, 10.19.

NMR (CDCl$_3$ solvent, TMS internal standard)

$^1$H NMR: δ1.32 (9H, s, CH$_3$), 1.62 (9H, s, CH$_3$), 3.69 (2H, s, CH$_2$, $^2$J($^{77}$Se-$^1$H)=12.0 Hz)

$^{13}$C NMR: δ26.1 ($^1$J($^{77}$Se-$^{13}$C)=52.2 Hz), 28.8, 29.1, 55.6, 62.2, 136.4, 172.6.

$^{77}$Se NMR (78.2 MHz, CDCl$_3$) δ247.9.

MS (CI): m/z=277 [M$^+$+1].

Thus, 3-t-butyl-2-t-butylimino-1,3-selenazolidin-4-one was confirmed to be a compound represented by chemical formula 10.

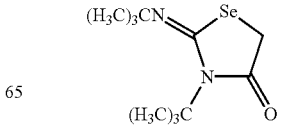

(10)

EXAMPLE 8

The reaction was carried out in the same manner as Example 1 except that N,N'-4-methylphenyl selenourea (2.0 mmol) was used instead of N,N'-diisopropyl selenourea for the selenourea. As a result, 3-p-tolyl-2-p-tolylimino-1,3-selenazolidin-4-one was obtained. The yield was 100%.

Elementary analysis, nuclear magnetic resonance spectrum and mass analysis of 3-p-tolyl-2-p-tolylimino-1,3-selenazolidin-4-one were as indicated below.

Elementary analysis: (C:H:N) Calcd. 59.48, 4.70, 8.16. Found 59.44, 4.73, 8.25.

NMR (CDCl$_3$ solvent, TMS internal standard)

$^1$H NMR: δ2.31 (3H, s, CH$_3$), 2.37 (3H, s, CH$_3$), 3.96 (2H, s, CH$_2$, $^2$J($^{77}$Se-$^1$H)=12.8 Hz), 6.79 (2H, d, J=7.8 Hz, Ar), 7.10 (2H, d, J=7.8 Hz, Ar), 7.22 (2H, d, J=8.0 Hz, Ar), 7.30 (2H, d, J=8.0 Hz, Ar).

13C NMR: δ20.9, 21.2, 25.1 ($^1$J($^{77}$Se-$^{13}$C)=70.3 Hz), 120.2, 127.7, 129.7, 130.1, 133.7, 134.3, 138.9, 146.9, 151.0, 173.1.

$^{77}$Se NMR (78.2 MHz, CDCl$_3$) δ264.9.

MS (CI): m/z=345 [M$^+$+1].

Thus, 3-p-tolyl-2-p-tolylimino-1,3-selenazolidin-4-one was confirmed to be a compound represented by chemical formula 11.

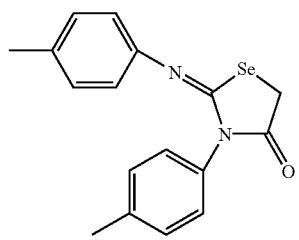

(11)

EXAMPLE 9

The reaction was carried out in the same manner as Example 1 except that N,N'-2-methylphenyl selenourea (2.0 mmol) was used instead of N,N'-diisopropyl selenourea for the selenourea. As a result, 3-o-tolyl-2-o-tolylimino-1,3-selenazolidin-4-one was obtained. The yield was 92%.

Elementary analysis, nuclear magnetic resonance spectrum and mass analysis of 3-o-tolyl-2-o-tolylimino-1,3-selenazolidin-4-one were as indicated below.

Elementary analysis: (C:H:N) Calcd. 59.48, 4.70, 8.16. Found 59.65, 4.81, 8.02.

NMR (CDCl$_3$ solvent, TMS internal standard)

$^1$H NMR: δ2.09 (3H, s, CH$_3$), 2.29 (3H, s, CH$_3$), 3.97 (2H, d, J=1.2 Hz, CH$_2$, $^2$J($^{77}$Se-$^1$H)=35.6 Hz), 6.80 (1H, dd, J=8.0, 1.2 Hz, Ar), 7.01 (1H, td, J=7.2, 1.6 Hz, Ar), 7.13 (2H, m, Ar), 7.23 (1H, m, Ar), 7.35 (3H, m, Ar).

$^{13}$C NMR: δ17.6, 17.7, 32.9, 119.7, 124.6, 126.4, 127.2, 128.5, 129.4, 129.7, 130.5, 131.2, 134.0, 136.0, 146.7, 153.8, 171.1.

MS (CI): m/z=345 [M$^+$+1].

Thus, 3-o-tolyl-2-o-tolylimino-1,3-selenazolidin-4-one was confirmed to be a compound represented by chemical formula 12.

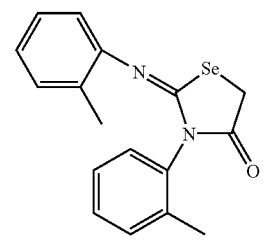

(12)

EXAMPLE 10

Action relative to a plurality of protein kinases was investigated in accordance with the method for simultaneous detection of the activity of a plurality of protein kinases on a single gel as described in Anal. Biochem. 212:106–110, 1993.

More specifically, NIH3T3 cells transformed with v-src were disintegrated with a hypotonic buffer and denucleated by gentle centrifugation. Various types of kinases (including 1 μM PMA (phorbolmyristate acetate), 20 μM cyclic adenosine-3',5'-monophosphate (cAMP)) were then added to the centrifuged supernatant. Moreover, 3-isopropyl-2-isopropylimino-1,3-selenazolidin-4-one of chemical formula 4 and labeled adenosine triphosphate (ATP) were added and the mixture was allowed to react. After stopping the reaction, the phosphorylated protein was analyzed by SDS-PAGE and autoradiography.

As a result, the 3-isopropyl-2-isopropylimino-1,3-selenazolidin-4-one was shown to have 20 times or more inhibitory activity compared with rottlerin typically used as a protein kinase inhibitor.

EXAMPLE 11

The growth inhibitory action of the selenazolin derivatives of chemical formulas 4 through 12 against human HT-1080 fibrosarcoma cells was investigated. HT-1080 fibrosarcoma cells growing in Eagle's Minimum Essential Medium (EMEM) containing 10% fetal calf serum within an incubator having an atmosphere of 5% CO$_2$ and 95% air maintained at a temperature of 37 degrees Celsius were inoculated into a 96-well plate at the rate of 1×10$^4$ cells/well. After 48 hours, the medium was replaced with Dulbecco's Modified Eagle's Medium (DMEM)/F12 medium containing 0.1% bovine serum albumin, and the test drugs at each concentration (0.1 μM, 100 μM) were added, followed by culturing for 24 hours. Growth inhibitory action on human HT-1080 fibrosarcoma cells was determined from the staining density following staining using the crystal violet method. Those results are shown in Table 1.

TABLE 1

| Chemical Formula | 4 | 5 | 6 | 7 | 8 | 9 | 10 | 11 | 12 |
|---|---|---|---|---|---|---|---|---|---|
| Growth Inhibitory (μM/IC$_{50}$) | 3.2 | >100 | 89.0 | 2.5 | 98.0 | >100 | 4.5 | >100 | 75.0 |

As shown in Table 1, the 1,3-selenazolin derivatives of chemical formulas 4, 7 and 10 exhibited potent growth inhibitory action on HT-1080 fibrosarcoma cells.

It should be apparent to those skilled in the art that the present invention may be embodied in many other specific forms without departing from the spirit or scope of the invention. Particularly, it should be understood that the present invention may be embodied in the following forms.

In each example, after allowing selenourea and α-haloacyl halide to react in a solvent, a catalyst was added to carry out the reaction in two stages. Alternatively, selenourea, α-haloacyl halide and a catalyst may be added to the solvent to carry out the reaction in a single step.

1,3-selenazolin derivatives may be used for germicides, antibacterial agents, antiviral agents and antibiotics corresponding to the physiological activity of the particular 1,3-selenazolin derivative.

The present examples and embodiments are to be considered as illustrative and not restrictive, and the invention is not to be limited to the details given herein, but may be modified within the scope and equivalence of the appended claims.

What is claimed is:

1. A 1,3-selenazolin compound of the chemical formula 1,

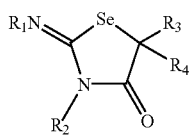

(1)

wherein the substitution groups R1 and R2 are mutually the same and are selected from the group consisting of isopropyl, cyclohexyl, t-butyl, p-tolyl, and o-tolyl; wherein when the substitution groups R1 and R2 are isopropyl, the substitution groups R3 and R4 are one of the following combinations:

hydrogen and hydrogen;
hydrogen and methyl;
methyl and methyl; or
hydrogen and phenyl;

wherein when the substitution groups R1 and R2 are cyclohexyl, the substitution groups R3 and R4 are hydrogen;
wherein when the substitution groups R1 and R2 are t-butyl, the substitution groups R3 and R4 are hydrogen;
wherein when the substitution groups R1 and R2 are p-tolyl, the substitution groups R3 and R4 are hydrogen; and
wherein when the substitution groups R1 and R2 are o-tolyl, the substitution groups R3 and R4 are hydrogen.

2. A process for preparing the 1,3-selenazolin compound of claim 1, the process comprising a step of reacting a selenourea represented by the following chemical formula 2 and an α-haloacyl halide represented by the following chemical formula 3 in a solvent and in the presence of a catalyst,

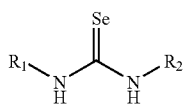

(2)

-continued

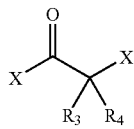

(3)

wherein X in the chemical formula 3 denotes halogen,
wherein the substitution groups R1 and R2 are mutually the same and are selected from the group consisting of isopropyl, cyclohexyl, t-butyl, p-tolyl, and o-tolyl; wherein when the substitution groups R1 and R2 are isopropyl, the substitution groups R3 and R4 are one of the following combinations:

hydrogen and hydrogen;
hydrogen and methyl;
methyl and methyl; or
hydrogen and phenyl;

wherein when the substitution groups R1 and R2 are cyclohexyl, the substitution groups R3 and R4 are hydrogen;
wherein when the substitution groups R1 and R2 are t-butyl, the substitution groups R3 and R4 are hydrogen;
wherein when the substitution groups R1 and R2 are p-tolyl, the substitution groups R3 and R4 are hydrogen; and
wherein when the substitution groups R1 and R2 are o-tolyl, the substitution groups R3 and R4 are hydrogen.

3. The preparation process according to claim 2, wherein the halogen is chlorine or bromine.

4. The preparation process according to claim 2, wherein the molar ratio of the α-haloacyl halide to the selenourea is 1:1.5 to 1:2.

5. The preparation process according to claim 2, wherein the reaction step is carried out at a reaction temperature of −100 to 30 degrees Celsius.

6. The preparation process according to claim 2, wherein the reaction step includes reacting the selenourea, the α-haloacyl halide and the catalyst at a time.

7. The preparation process according to claim 2, wherein the reaction step includes:

a first step of reacting the selenourea and the α-haloacyl halide in a solvent, and
a second step of adding the catalyst followed by the further reaction of the selenourea and the α-haloacyl halide.

8. The preparation process according to claim 2, wherein the catalyst is a catalyst selected from a metal catalyst, Lewis acid catalyst, basic catalyst and enzyme.

9. A medicament containing a 1,3-selenazolin compound of the chemical formula 1,

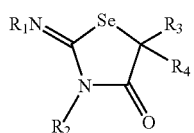

(1)

wherein the substiotution groups R1 and R2 are mutually the same and are selected from the group consisting of isopropyl, cyclohexyl, t-butyl, p-tolyl, and o-tolyl; wherein when the substitution groups R1 and R2 are isopropyl, the substitution groups R3 and R4 are one of the following combinations:

hydrogen and hydrogen;
hydrogen and methyl;
methyl and methyl; or
hydrogen and phenyl;
wherein when the substitution groups R1 and R2 are cyclohexyl, the substitution groups R3 and R4 are hydrogen;
wherein when the substitution groups R1 and R2 are t-butyl, the substitution groups R3 and R4 are hydrogen;
wherein when the substitution groups R1 and R2 are p-tolyl, the substitution groups R3 and R4 are hydrogen; and
wherein when the substitution groups R1 and R2 are o-tolyl, the substitution groups R3 and R4 are hydrogen.

10. An agricultural chemical composition containing a 1,3-selenazolin compound of the chemical formula 1,

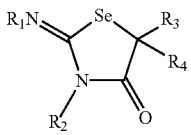

(1)

wherein the substiotution groups R1 and R2 are mutually the same and are selected from the group consisting of isopropyl, cyclohexyl, t-butyl, p-tolyl, and o-tolyl; wherein when the substitution groups R1 and R2 are isopropyl, the substitution groups R3 and R4 are one of the following combinations:

hydrogen and hydrogen;
hydrogen and methyl;
methyl and methyl; or
hydrogen and phenyl;
wherein when the substitution groups R1 and R2 are cyclohexyl, the substitution groups R3 and R4 are hydrogen;
wherein when the substitution groups R1 and R2 are t-butyl, the substitution groups R3 and R4 are hydrogen;
wherein when the substitution groups R1 and R2 are p-tolyl, the substitution groups R3 and R4 are hydrogen; and
wherein when the substitution groups R1 and R2 are o-tolyl, the substitution groups R3 and R4 are hydrogen.

* * * * *